US00PP27600P3

(12) United States Plant Patent
Lee

(10) Patent No.: US PP27,600 P3
(45) Date of Patent: Jan. 24, 2017

(54) ***GARDENIA* PLANT NAMED 'LEEFOUR'**

(50) Latin Name: *Gardenia hybrida*
Varietal Denomination: LEEFOUR

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 166 days.

(21) Appl. No.: 14/121,172

(22) Filed: Aug. 11, 2014

(65) Prior Publication Data

US 2016/0044848 P1 Feb. 11, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Keith Robinson

(74) *Attorney, Agent, or Firm* — Cassandra Bright

(57) ABSTRACT

A new and distinct *Gardenia* cultivar named 'LEEFOUR' is disclosed, characterized by a upright growth habit and suitability for Southern climates. The new cultivar is a *Gardenia*, suitable for ornamental garden purposes.

2 Drawing Sheets

Latin name of the genus and species: *Gardenia hybrida.* Variety denomination: 'LEEFOUR'.

BACKGROUND OF THE INVENTION

The new cultivar is a product of a planned breeding program by the inventor. This new variety, hereinafter referred to as 'LEEFOUR', was found as an openly pollinated seedling in a group of *Gardenia jasminoides* 'Daisy' (unpatented) seedling plants being grown in Independence, La. The inventor, Robert Edward Lee, discovered the seedling in Independence, Louisiana, at a research nursery during October of 2000.

After identifying the new variety as a potentially interesting selection, the inventor first organized propagation of 'LEEFOUR' by vegetative cuttings during 2004 at the same commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEEFOUR' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEEFOUR' These characteristics in combination distinguish 'LEEFOUR' as a new and distinct *Gardenia* cultivar:

1. Upright, vigorous growth habit.
2. Tolerance for heat and disease
3. Adaptability to production and use in Southern climates.

4. Excellent flower fragrance.
5. Extremely compact growth
6. Deep green, shiny foliage
7. Good specimen plant
8. Good container plant

COMPARISON TO PARENT VARIETY

'LEEFOUR' is similar in most horticultural characteristics to the seed parent variety *Gardenia* 'Daisy' unpatented. Plants of the new cultivar 'LEEFOUR' however, are larger and grow faster than plants of 'Daisy'.

The pollen parent is unknown.

COMMERCIAL COMPARISON

'LEEFOUR' can be compared to the commercial variety *Gardenia* hybrid 'LEETWO', U.S. Plant patent application Ser. No. 14/121,171, filed concurrently. Plants of the new cultivar 'LEEFOUR' are similar to plants of 'LEETWO' in most horticultural characteristics, however, plants of the new cultivar 'LEEFOUR' produce larger flowers and overall plant size of 'LEEFOUR' is larger and the shape more upright.

BRIEF DESCRIPTION OF THE PHOTOGRAPHS

Figure 1:
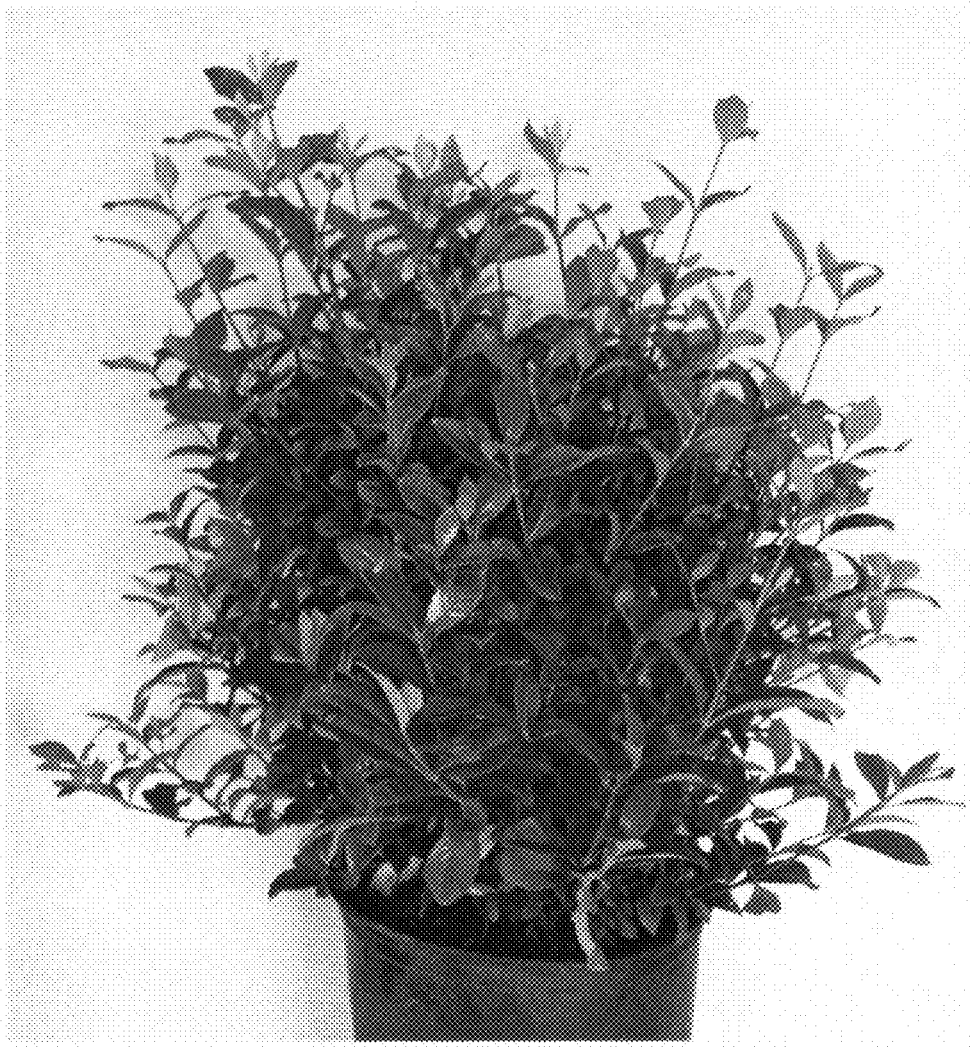

The accompanying photograph in FIG. 1 illustrates in full color a plant of 'LEEFOUR' grown outdoors in Alabama.

Figure 2:
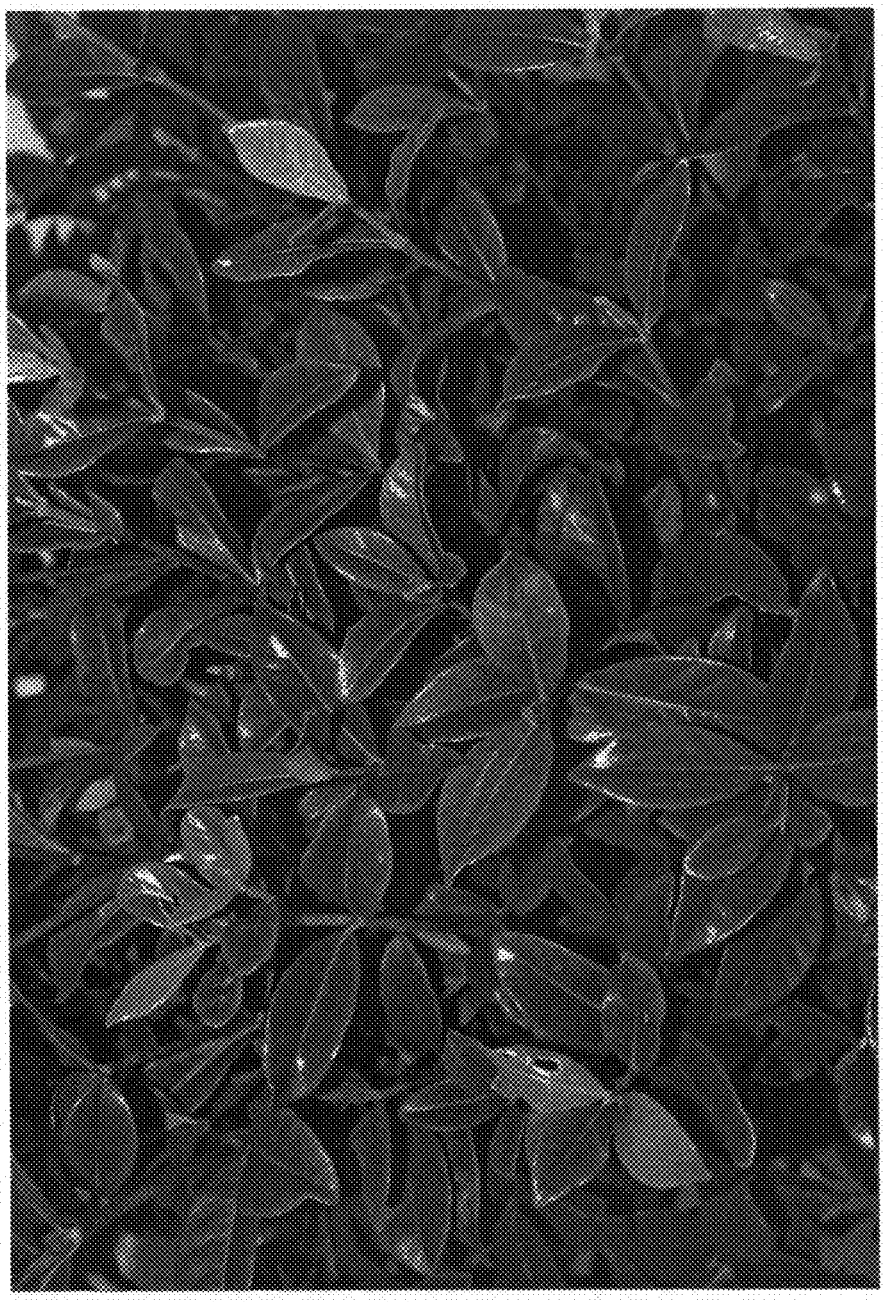

FIG. 2 shows a close up of a typical foliage of the new variety. The plant is approximately 2 years old, and is shown in a three gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LEEFOUR' plants grown outdoors in Loxley, Ala. Plants are approximately 3 years old, in a 3 gallon nursery container. Measurements and numerical values represent averages of typical plant types.

Botanical classification: *Gardenia hybrid* 'LEEFOUR'.

PROPAGATION

Typically by semi-hardwood cuttings in Spring and Summer.

Root description: Woody to semi-woody. Colored near RHS Brown 200D. Moderately dense and moderately freely branching.

Time to initiate roots: About 4 to 6 weeks in the Summer.

Time to produce a rooted young plant: Approximately 12 weeks in the Summer.

PLANT

Growth habit: Upright, somewhat globular shrub.

Height: Approximately 60 cm to top of foliar and flowering plane.

Plant spread: Approximately 50 cm.

Branching characteristics: Well branched, approximately 4 to 6 lateral branches emerge from a pinch. Branches occur at approximately 15° angles.

Primary branches:

- *Length of primary branches.*—Average 20 cm, then pinched and new branches emerge.
- *Diameter of primary branches.*—Approximately 0.6 cm.
- *Primary branch strength.*—Very strong, flexible difficult to break.
- *Primary branch color.*—Mature branches near RHS Greyed-Green 197A. Young branches near Grey-Brown N199A.
- *Primary branch texture.*—Mature branches slightly rough and slightly striated. Young growth slightly pubescent.

Lateral branches:

- *Color.*—Near Grey-Brown N199A.
- *Length.*—Average range 9 cm to 30 cm.
- *Diameter.*—Average 0.5 cm.
- *Aspect.*—Straight, attached at acute angles.
- *Texture.*—Scaly.
- *Strength.*—Very strong, somewhat flexible.
- *Internode.*—Average range 1.8 to 4.2 cm.

Age of plant described: Approximately 2 years.

FOLIAGE

Leaf:

- *Type.*—Simple.
- *Arrangement.*—Opposite.
- *Average length.*—Approximately 6.0 cm.
- *Average width.*—Approximately 2.8 cm.
- *Shape of blade.*—Somewhat broad elliptic.
- *Apex.*—Acute.
- *Base.*—Broad attenuate.
- *Attachment.*—Sessile.
- *Margin.*—Entire.
- *Texture of top surface.*—Glabrous.
- *Texture of bottom surface.*—Glabrous.
- *Appearance of top surface.*—Very glossy.
- *Appearance of bottom surface.*—Matte.
- *Color.*—Young foliage upper side: Near RHS Yellow-Green 144A, but darker. Young foliage under side: Near RHS Green 138B. Mature foliage upper side: Near RHS Green 139A. Mature foliage tinder side: Near RHS Green 138B.

Venation:

- *Type.*—Pinnate.
- *Venation color upper side.*—Near RHS Yellow-Green 144C.
- *Venation color under side.*—Near RHS Yellow-Green 145B.

FLOWER

Bloom period: Plants flower in the Spring, then begin intermittent flowering cycles in late Spring/Summer through Fall.

Inflorescence:

- *Arrangement.*—Semi-double flowers arise from upper leaf axils.

Peduncle:

- *Length.*—Average 0.8 cm.
- *Diameter.*—0.4 cm.
- *Color.*—Near RHS Green 143C.
- *Texture.*—Glabrous.
- *Aspect.*—Straight.
- *Strength.*—Moderately strong, flexible.

Flowers:

- *Length.*—Average 3.9 to 4.7 cm.
- *Diameter.*—Average range 5.5 to 7.0 cm.
- *Facing direction.*—Outwardly and upwardly facing.
- *Persistent or self-cleaning.*—Persistent.
- *Fragrance.*—Very strong sweet fragrance.

Tube:

- *Description.*—Tube section of corolla is very tightly held by calyx.
- *Tube length.*—Approximately 1.8 to 2.4 cm.
- *Tube width a widest point.*—Approximately 1.1 cm.
- *Tube width and narrowest point.*—Approximately 0.6 cm.
- *Color.*—Inner: Near RHS Yellow 10D. Outer: Near RHS Yellow 10D.

Petals:

- *Quantity.*—12 to 18 fully formed petals. 3 to 7 reduced, irregularly shaped and sized petaloids in the interior of the flower.
- *Unfused petal segments.*—Length: Average range 2.5 to 3.5 cm. Width: Average 1.5 cm.
- *Apex.*—Rounded, occasionally very shallow irregular lobes.
- *Shape of petal.*—Obovate.
- *Petal margin.*—Entire.
- *Petal arrangement.*—Whorled, fused approximately ⅕ from base.
- *Petal texture.*—Smooth all surfaces.

Color:

- *Upper surface at first opening.*—Near RHS White 155A, lightly flushed Yellow 10D.
- *Under surface at first opening.*—Near RHS White 155A, lightly flushed Yellow 10D.
- *Inner surface at maturity.*—Near RHS White 155A, heavily flushed Yellow 10D. Interior petals have a basal blotch near Yellow 13B.

*Outer surface at maturity*.—Near RHS White 155A, heavily flushed Yellow 9D. Basal blotch near Yellow 13B. Occasional marginal blotching Yellow 13C.

*Upper surface at fading*.—Near RHS Yellow 10D.

*Under surface at fading*.—Near RHS Yellow 10D, streaking throughout near Yellow 9A and yellow 13B.

Bud:

*Shape*.—Elliptic.

*Length*.—Average 4.0 cm.

*Diameter*.—2.5 cm.

*Color*.—Near RHS White 155C and Yellow 10D.

Calyx/sepals:

*Quantity per flower*.—5 sepals.

*Shape*.—Narrow deltate, base fused.

*Length*.—Average 2.5 cm.

*Width*.—Sepal 0.2 cm, calyx 2.2 at widest point.

*Apex*.—Acute.

*Base*.—Fused.

*Margin*.—Entire.

*Texture*.—Glabrous all surfaces. Color: Inner Surface: Near RHS Green 143C. Outer Surface: Near RHS Yellow-Green 144A.

REPRODUCTIVE ORGANS

Stamens:

*Number*.—3 observed. Androeceium fused to floral tube, except anthers. Anthers misshapen and irregular.

*Length*.—0.07 cm, anthers only.

*Width*.—0.1 cm.

*Anthers*.—Anthers reflexed back, and attached to petals. Length: Approximately 0.7 cm. Shape: Crescent. Color: Near RHS Greyed-Orange 163CB, turning 164A with age. Pollen: Pollen not observed to be produced.

Pistil:

*Number*.—1, somewhat misshapen.

*Length*.—2.5 cm.

*Style*.—Length: 1.2 cm. Color: Near RHS Green-White 155C.

*Stigma*.—3 lobed elongated globular, colored near Yellow 9C.

*Ovary*.—Approximately 0.3 cm in diameter, irregularly shaped 0.3 long. Colored near Yellow-Green 1C.

OTHER CHARACTERISTICS

Disease and pest resistance: Observed to be more resistant to normal diseases and pests of *Gardenia hybrida*. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: USDA Zone 8.

Fruit/seed production: Not observed to date.

What is claimed is:

1. A new and distinct cultivar of *Gardenia* plant named 'LEEFOUR' as herein illustrated and described.

* * * * *